United States Patent
Natalicio

(10) Patent No.: US 6,217,534 B1
(45) Date of Patent: *Apr. 17, 2001

(54) METHOD AND PULSATING SPRAY APPARATUS FOR INDUCING ALTERED STATES IN HUMAN BEINGS

(76) Inventor: John C. Natalicio, 2600 Griffith Park Blvd., Los Angeles, CA (US) 90039

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/895,401

(22) Filed: Jul. 16, 1997

Related U.S. Application Data

(63) Continuation of application No. 08/516,979, filed on Aug. 18, 1995, now abandoned, which is a continuation-in-part of application No. 08/189,297, filed on Jan. 31, 1994, now abandoned, which is a continuation of application No. 07/980,107, filed on Nov. 23, 1992, now abandoned, which is a continuation of application No. 07/669,119, filed on Mar. 12, 1991, now abandoned.

(51) Int. Cl.[7] ............................. A61H 9/00; B05B 1/08; F16K 15/14
(52) U.S. Cl. ...................... 601/155; 601/160; 601/169; 239/99; 137/853
(58) Field of Search .................. 239/11, 93, 99, 239/101, 380, 381, 389, 255, 337, 700; 4/542; 128/24.1, 64–66; 601/154, 155, 160, 169; 138/30

(56) References Cited

U.S. PATENT DOCUMENTS

| | | | | |
|---|---|---|---|---|
| 3,801,019 | * | 4/1974 | Trenary | 239/383 |
| 3,861,383 | * | 1/1975 | Kovach | 128/66 |
| 3,870,039 | * | 3/1975 | Moret | 128/66 |
| 3,924,805 | * | 12/1975 | Nebeker | 239/381 |
| 3,985,303 | * | 10/1976 | Steimle | 128/66 |
| 4,139,001 | * | 2/1979 | Macabee | 128/66 |
| 4,278,078 | * | 7/1981 | Smith | 128/66 |
| 4,282,866 | * | 8/1981 | Miffitt | 128/66 |
| 4,834,288 | * | 5/1989 | Kenny | 239/99 |
| 4,863,101 | * | 9/1989 | Pater | 239/99 |
| 4,892,106 | * | 1/1990 | Gleeson | 128/745 |
| 5,014,372 | * | 5/1991 | Thrasher | 4/542 |

* cited by examiner

Primary Examiner—Danton D. DeMille

(57) ABSTRACT

A method for inducing a state of conciousness in a human being by bombarding the body with a fluid pulsating at a frequency corresponding with the frequency of brainwaves normal to the state being induced. A method is also disclosed for producing a concentrated fluid discharge by completely and rapidly blocking a flowing fluid stream under pressure, accumulating the resulting pressure rise and completely and rapidly releasing a concentrated fluid pulse. The invention includes apparatus for a producing a cyclic fluid discharge with a frequency from ½ to 120 pulses per second. Another method is disclosed for reducing fluid consumption without restricting fluid passageways by cyclically interrupting the flow of fluid and controlling the percentage of time during each cycle that fluid is allowed to flow.

16 Claims, 12 Drawing Sheets

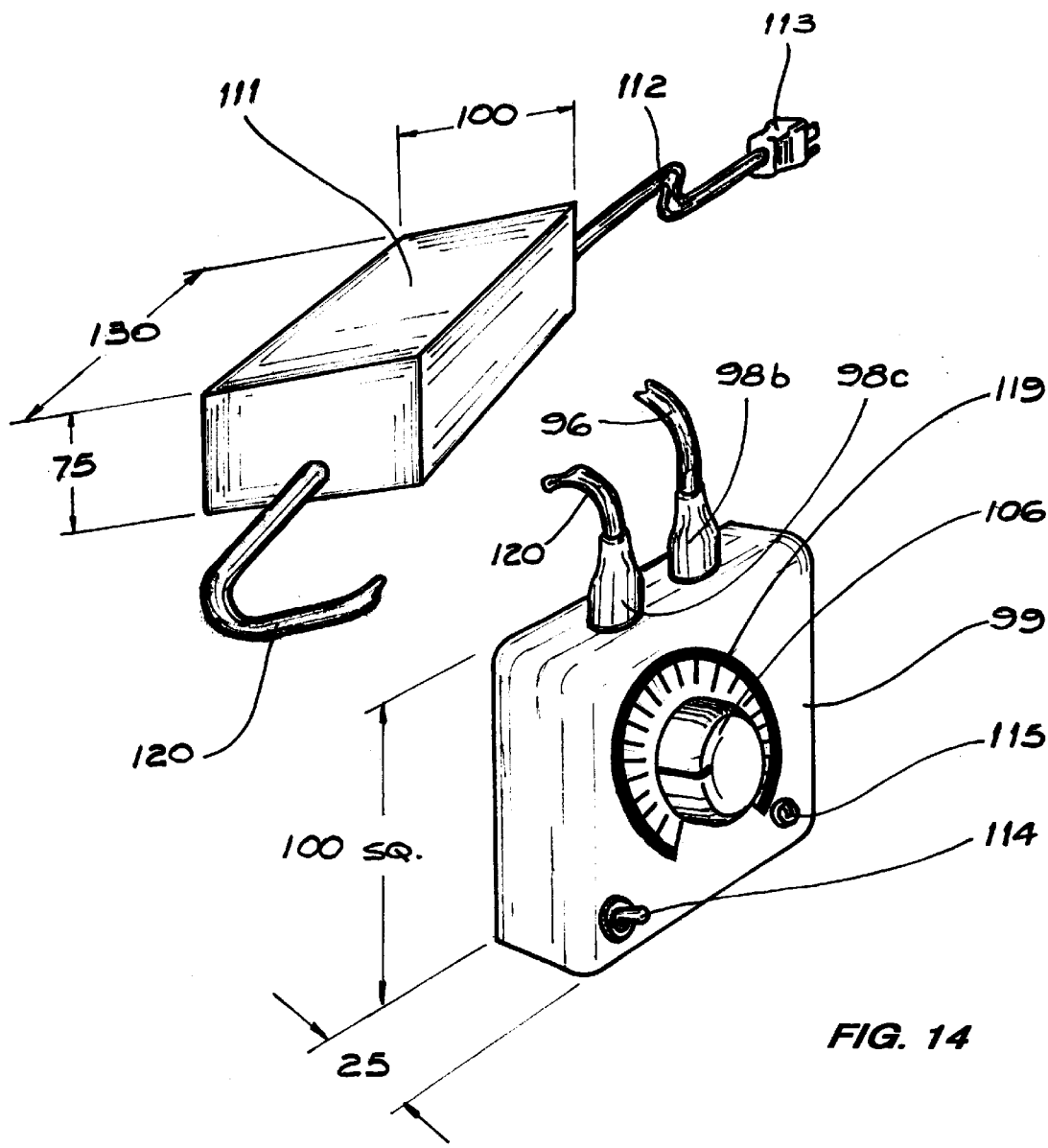

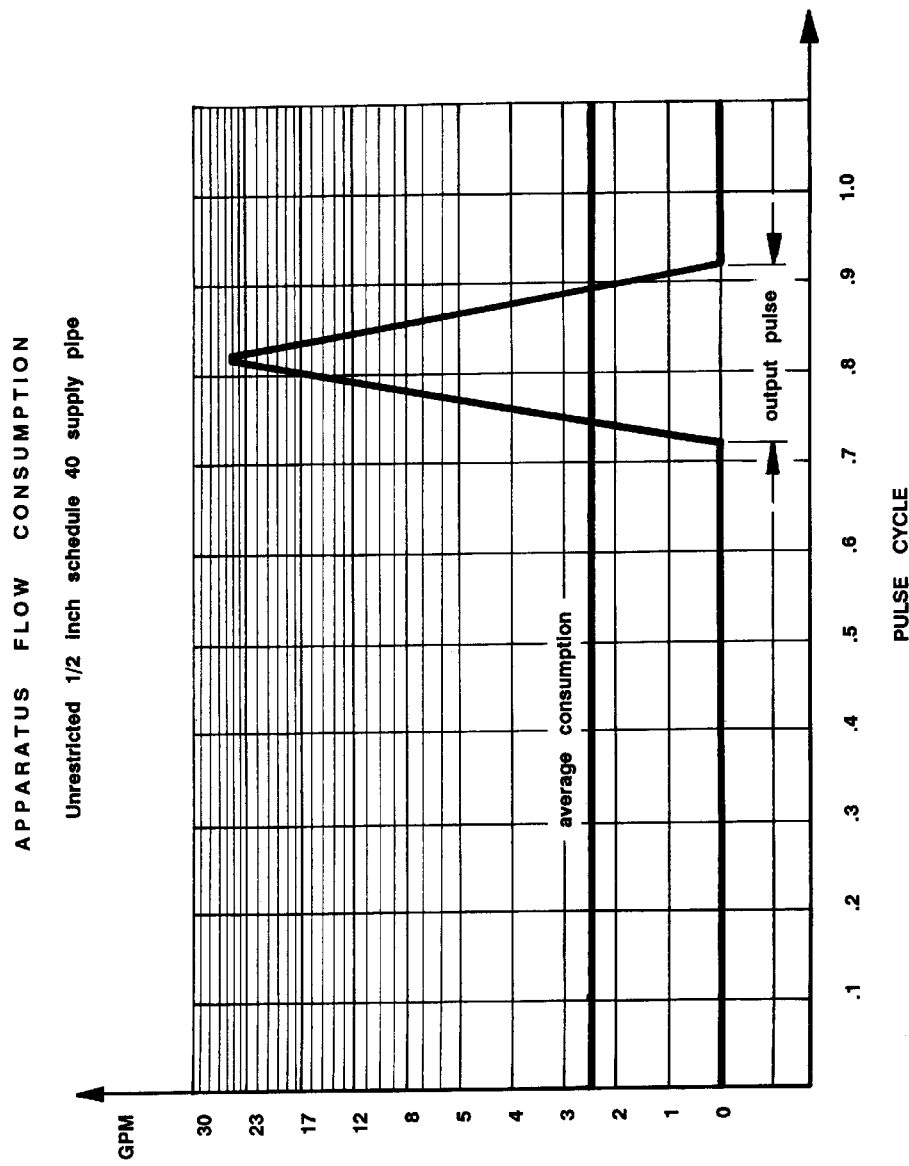

METHOD AND PULSATING SPRAY APPARATUS FOR INDUCING ALTERED STATES IN HUMAN BEINGS

CROSS-REFERENCE TO RELATED APPLICATIONS

This is a continuation of application Ser. No. 08/516,979 filed Aug. 18, 1995 now abandoned, which is a continuation-in-part of application Ser. No. 08/189,297 filed Jan. 31, 1994 now abandoned, which is a continuation of application Ser. No. 07/980,107 filed Nov. 23, 1992 now abandoned, which is a continuation of application Ser. No. 07/669,119 filed Mar. 12, 1991 now abandoned.

BACKGROUND—FIELD OF INVENTION

The present invention is a method for producing altered states in human beings wherein the appellation "altered states" denotes a change in consciousness from an existing state to another, within the context of the scientific discovery by Hans Berger in 1929, which documented the human brain giving off electrical energy in distinct, measurable patterns.

Decades of research have verified such patterns as corresponding to specific states of consciousness, measurable in cycles per second and categorized according to frequency as: Delta, Theta, Alpha and Beta.

Delta frequencies range from one to three cycles per second, Theta from four to seven, Alpha from eight to thirteen and Beta from fourteen to thirty and beyond.

All human beings and nearly all mammals share these patterns with minor variations among individuals.

Delta, is prominent in the deepest stages of sleep. Theta, is related to creativity, dream activity and relaxation. Alpha, is characterized by a relaxed but awake state of mind. Beta, is the brainstate of an awake and alert consciousness.

In 1975, in the context of stress research, J. Stoyva determined the occurrence of Theta activity in the brain as an indication of a state of consciousness incompatible with anxiety. Research further indicates that parts of the body other than the brain may be used to induce the manifestation of particular brainwaves.

To produce altered states in human beings, a method embodying the present invention comprises externally inducing the frequency common to the desired state on the physical body of a human being by means of precisely adjustable pulsating fluid sprays capable of a range of frequencies varying from ½ to 120 pulses per second.

BACKGROUND—DESCRIPTION OF PRIOR ART

In the art of pulsating fluid or water spray devices, such as disclosed in U.S. Pat. Nos. 3,762,648, 3,801,019, 4,010,899, 4,068,801, 4,141,502, 4,204,646, 4,330,089, 4,346,844, 4,579,284, 4,558,130, and 4,754,928, the predominant common feature is that the various means of producing fluid pulsation are water driven.

A drawback of these spray devices is that they consume part of the water's energy to operate. Another drawback is their lack of intent and ability to match the range of frequencies common to brainwaves. A further drawback, owing to these devices dependance on water flow and pressure to operate, is the unpredictable performance from one dwelling to another.

A water supply line 100 feet in length, or the equivalent combination of pipe lengths and fittings found in most households, will deliver, under a head of 115 feet of water, 9 gallons per minute at a velocity of 9 feet per second and 0 psig dynamic pressure.

Installing a spray apparatus compliant with water consumption regulations on this supply line would limit output flow to 2½ gallons per minute, reduce the fluid velocity to 2.6 feet per second and restore dynamic pressure within 10% to 15% of the initial head.

This 10% to 15% pressure loss results from fluid friction in the supply line. Known spray apparatus cannot recover this loss.

Some spray apparatus suffer the further drawback of causing an effect known as water hammer in the supply line when they operate. Water hammer can loosen and damage pipes and free sediments that clog fittings and fixtures attached to the line.

Other water driven spray apparatus incurr additional pressure losses aerating the fluid or diverting it through complex mechanisms essentially designed to present the supply pipeline with a constant fluid demand in order to avoid water hammer. The drawback of these mechanisms is that they are incapable of capturing the latent energy in the fluid stream.

Yet another further drawback of present spray apparatus is the reduction of fluid consumption by means that restrict flow. Internal restrictions consume fluid energy across small orifices or activating various mechanisms. Restrictions at the nozzle result in high discharge velocities out of small channels or orifices, giving the user the feeling of being stung by needles.

Some spray apparatus resort to increased size or number of orifices to reduce fluid velocity. This increases fluid consumption, mandating an internal flow restriction which in turn produces a bland discharge. Other spray apparatus aerate the discharge stream to compensate for its high velocity as well as to avoid watter hammer.

These solutions are not satisfactory to the user, as the resulting pulsating spray exhibits a much reduced force, or a noticeable lack of water flow and sometimes both.

In the Spray Nozzle disclosed in U.S. Pat. No. 3,762,648, the invention is specially directed to produce a pulsating or intermitently interrupted spray with no variations in back pressure in order to eliminate water hammer, and to produce an adjustable rate of pulsation that is independent from the pressure of the water supply.

A drawback to this method is that it is dependent on the fluid stream, dividing its energy between two flow paths, to maintain an even flow and thus eliminate water hammer. Another drawback is that being water powered, it uses part of the fluid's energy to operate its internal mechanisms. A further drawback is that it changes the pulse rate by proportionally dividing flow and pressure between the two flow paths, so that as the number of pulses increases, the force of the output spray decreases.

Another further drawback to this method is that presenting the supply line with no variations in back pressure constitutes what is essentialy a steady state, without possibility of realizing the kinetic energy latent in the fluid stream.

In the Skin Massaging Instrument disclosed in U.S. Pat. No. 3,861,383, the invention is directed to the treatment of a confined area of the skin, not exceeding 1½ square inches, with a water jet pulsating between 2,200 and 3,200 cycles per minute, with an impingement velocity on the skin between 9 to 18 feet per second. The apparatus contains an electric motor driving a piston pump and fluid reservoir, and confines its action by means of a rim pressed against the skin.

A drawback of such method is that the effective area is confined in order for effective action to take place. A further drawback is that its operating pulse frequency is many times that which is normal to brainwaves. Another drawback is that the fluid becomes contaminated from skin and hair particles in constant recirculation. Another further drawback is that it cannot operate from a standard supply pipeline.

In the Lavage Handpiece Apparatus disclosed in U.S. Pat. No. 4,278,078, the generation of fluid pulsations consists of an air powered pumping mechanism driving an eccentric crank, rod, and flat piston to cyclically squeeze a fluid filled flexible tube. The fluid overcomes the resistance of a downstream check valve and exits from a discharge nozzle as a fluid pulse. The apparatus uses a pinch valve to control inlet flow to the pumping area.

The drawback to this method is that an increase in the cycle rate produces an increase in the discharge velocity of the fluid and a corresponding increase in fluid consumption. A further drawback is that the cycling rate is limited by the recovery rate of the flexible tubing after it is deformed by the piston. Another drawback is that restricting the inlet flow also affects the recovery of the flexible tube. Another further drawback is the short life of the flexible tube at high cycling rates.

In the Method And Apparatus For Producing And Utilizing Percussive Liquid Jets, disclosed in U.S. Pat. No. 3,924,805, the generation of fluid pulsation consists of means of producing small cyclic variations of the discharge velocity of a continuous, uninterrupted liquid jet stream discharging from a single nozzle orifice, at elevated pressures and cycling rates, in the order of 1000 psig minimum, and at least 1000 cycles per second.

The drawback to this method is the effective range of its output, limited to approximately 4 inches, and the dangerous nature of the pressure it requires to function. Reducing the supply pressure to the level found in households and other residences renders its output completely inefective, while its cyclic frequency is many times beyond the sensory range of human beings.

In the Multiple Afferent Sensory Stimulation Device disclosed in U.S. Pat. No. 4,892,106, a a reproducing device emits sound and light signals for the purpose of audio and visual sensory stimulation for achieving mental and physical effects on a subject person.

A drawback of this device is that it confines its influence to sound and sight. Another drawback is its inability to remove physical stress from the body. A further drawback is the use of prerecorded source material, so that the program or pattern is set and cannot be changed. Another further drawback is that its use requires additional time and place set aside for it, something that individuals with a busy schedule may have trouble with.

Until the present invention, existing methods of producing discharge sprays have compromised contradictory requirements. To produce a strong pulsating spray the fluid stream must be fully and forcefully interrupted, yet the more accomplished the interruption, the more violent and destructive becomes the energy thus created in the supply lines.

The solutions demonstrated in the prior art focus on avoiding an ostensible problem without attempting to contain the source of the problem or harness its potentially destructive energy.

Water driven shower spray apparatus are designed to ameliorate pulsating shock and fluid consumption through partial flow interruptions, fluid diversions and aerating schemes. As a result, they share a characteristic feature; The energy of their discharge output is always less than the energy available at the inlet port.

The present invention reverses this conditions. Operating independently of the fluid supply, limiting fluid consumption without restricting fluid flow and accumulating the kinetic energy of the fluid stream, the apparatus releases a concentrated fluid pulse that exceeds the dynamic pressure available at the inlet port. Further, precise control of output pulse frequencies from ½ to 120 Hertz in half pulse increments allows the user to self induce brainwave frequencies corresponding to specific states of conciousness.

OBJECTS AND ADVANTAGES

Accordingly, besides the objects and advantages of the method and apparatus described in my above patent, several objects and advantages of the present invention are:

(a) to provide a reliable and consistent method for producing change from one state of consciousness to another.

(b) to provide a method for inducing change in a human being from one state of consciousness to another in a convenient manner, easily made part of a daily routine.

(c) to provide a method for inducing change from one state of consciousness to another that can be used at home.

(d) to provide a pulsating fluid spray apparatus which operates independently of the fluid supply for its pulsating operation.

(e) to provide a pulsating fluid spray apparatus which harnesses the fluid stream peak energy and converts it into a concentrated spray pulse.

(f) to provide the strongest possible fluid spray body massage for the user out of a common household water supply pipe.

(g) to provide a pulsating fluid spray apparatus which will not shake under the force of a strong pulsating discharge.

(h) to provide a pulsating fluid spray apparatus in which the user can choose the exact frequency of pulsation desired.

(i) to provide a pulsating fluid spray apparatus which is powered and controlled by a safe, low voltage power supply.

(j) to provide a pulsating fluid spray apparatus which has redundant insulation and a ground fault interrupt circuit preceding its power supply.

(k) to provide a pulsating fluid spray apparatus which lends itself to be operated under a fully programmable computerized control.

(l) to provide a pulsating fluid spray apparatus which can produce a continuous, non pulsating fluid discharge.

(m) to provide a pulsating fluid spray apparatus which has a constant fluid flow regardless of the rate of pulsation.

(n) to provide a pulsating fluid spray apparatus with reduced fluid consumption which does not diminish the fluid's energy.

(o) to provide a pulsating fluid spray apparatus which does not restrict the fluid flow.

(p) to provide a pulsating fluid spray apparatus which when producing a pulsating or continuous fluid discharge, meets all applicable City, State and upcoming Federal water use standards.

(q) to provide a pulsating fluid spray apparatus which would not be desireable to or easily tampered with to alter its fluid flow.

(r) to provide a pulsating fluid spray apparatus which has a wide range of directional adjustment of its discharge spray.

(s) to provide a pulsating fluid spray apparatus which allows the user to remove the discharge nozzle without tools.

(t) to provide a pulsating fluid spray apparatus which can accept different types of interchangeable discharge nozzles.

(u) to provide a pulsating fluid spray apparatus which has a minimum number of moving parts.

(v) to provide a pulsating fluid spray apparatus which requires minimum or zero maintenance by the user.

(w) to provide a pulsating spray apparatus which can be installed by the average person with minimal skills and with common household tools.

(x) to provide a pulsating fluid spray apparatus which is attractive to the user and mounts on standard shower installations.

(y) to provide a pulsating spray apparatus which has a threaded adaptor to facilitate mounting in a wide range of installations.

(z) to provide a pulsating spray apparatus which can be mass produced with existing methods and technology.

(aa) to provide a pulsating spray apparatus which if desired can be manually turned on to a continuous spray without power from its power supply.

Further objects and advantages are to provide an apparatus which can be used easily and conveniently to shower daily, which can produce a state of consciousness that is supportive of the daily activities of a human being, which can produce a profound, ready for sleep relaxation, or a relaxed and lucid state, or further, a relaxed and fully energized state. Other objects and advantages will become apparent from a consideration of the ensuing description and drawings.

DRAWING FIGURES

The preceding and other features of the invention will be fully understood from the following detailed descriptions and the accompanying drawings, in which:

FIG. 13 is a perspective drawing of the control housing.

FIG. 14 is a perspective drawing of the dc power supply.

FIG. 17 is a graph showing average and peak fluid consumption of the spray apparatus when supplied by an unrestricted pipeline.

Figure 1:
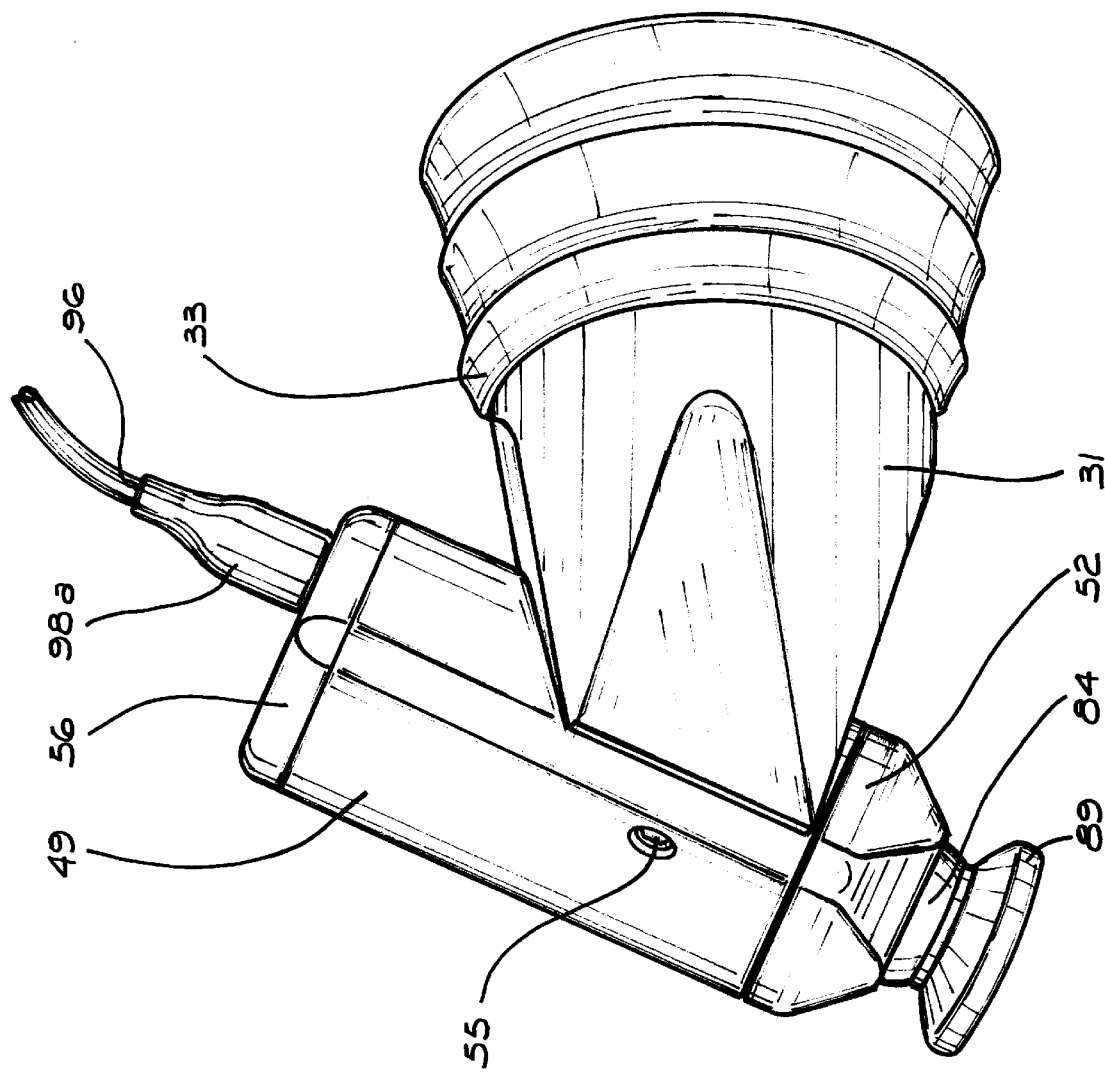
FIG. 1 is a perspective drawing of the apparatus exterior.

| Reference Numerals in Drawings | |
|---|---|
| 30 | pulsating spray apparatus |
| 31 | outer shell |
| 32 | outlet port |
| 33 | stabilizing ring |
| 34 | isolator ring |
| 35 | back up pad |
| 36 | end cover |
| 37 | threaded inlet port |
| 38 | O-ring |
| 39 | isolator washer |
| 40 | back up ring |
| 41 | retaining ring |
| 42 | retaining seal |
| 43 | end cap |
| 44 | end cap slots |
| 45 | flexible membrane housing |
| 46 | flexible membrane |
| 47 | membrane spacer |
| 48 | gasket |
| 49 | motor housing |
| 50 | motor housing inlet port |
| 51 | motor housing vent hole |
| 52 | retainer nut |
| 53 | spherical surface |
| 55 | motor housing fastener |
| 56 | rear cover |
| 57 | symmetrical stops |
| 58 | rear cover fastener |
| 59 | bulkhead spacer |
| 60 | vent passageway |
| 61 | locating hole |
| 62 | locating setscrew |
| 63 | O-ring |
| 64 | shaft seal |
| 65 | stepping motor |
| 66 | motor shaft |
| 67 | shaft flat |
| 68 | shaft hole |
| 69 | one way clutch |
| 70 | motor pressure pad |
| 71 | stationary sleeve |
| 72 | sleeve porting slot |
| 73 | sleeve locating hole |
| 74 | preload spring |
| 75 | O-ring |
| 76 | spherical surface |
| 77 | fluid chamber |
| 78 | rotating inner sleeve |
| 79 | inner sleeve porting slot |
| 80 | driving hole |
| 81 | flexible driver |
| 82 | driving pin |
| 83 | cross pin |
| 84 | spherical swivel joint |
| 85 | isolating insert |
| 86 | threaded insert |
| 87 | O-ring |
| 88 | access hole |
| 89 | discharge nozzle |
| 90 | check disc |
| 91 | circular groove |
| 92 | nozzle passageway |
| 93 | O-ring |

-continued

| | Reference Numerals in Drawings |
|---|---|
| 94 | male connector |
| 95 | connector spacer |
| 96 | motor cable |
| 97 | female connector-motor cable |
| 98 | safety boot |
| 99 | control housing |
| 100 | back plate |
| 101 | circuit board |
| 102 | potentiometer |
| 103 | washer |
| 104 | nut |
| 105 | O-ring |
| 106 | control knob |
| 107 | setscrew |
| 108 | back plate fastener |
| 109 | female connector-dc power |
| 110 | male connector- dc power |
| 111 | dc power supply |
| 112 | ac power cable |
| 113 | ac plug |
| 114 | selector switch |
| 115 | pilot light |
| 116 | threaded adaptor pipe |
| 117 | adhesive tape pad |
| 118 | expansion chamber |
| 119 | graduated dial plate |
| 120 | dc power supply |

DESCRIPTION—FIGS. 1 to 7

Figure 2:
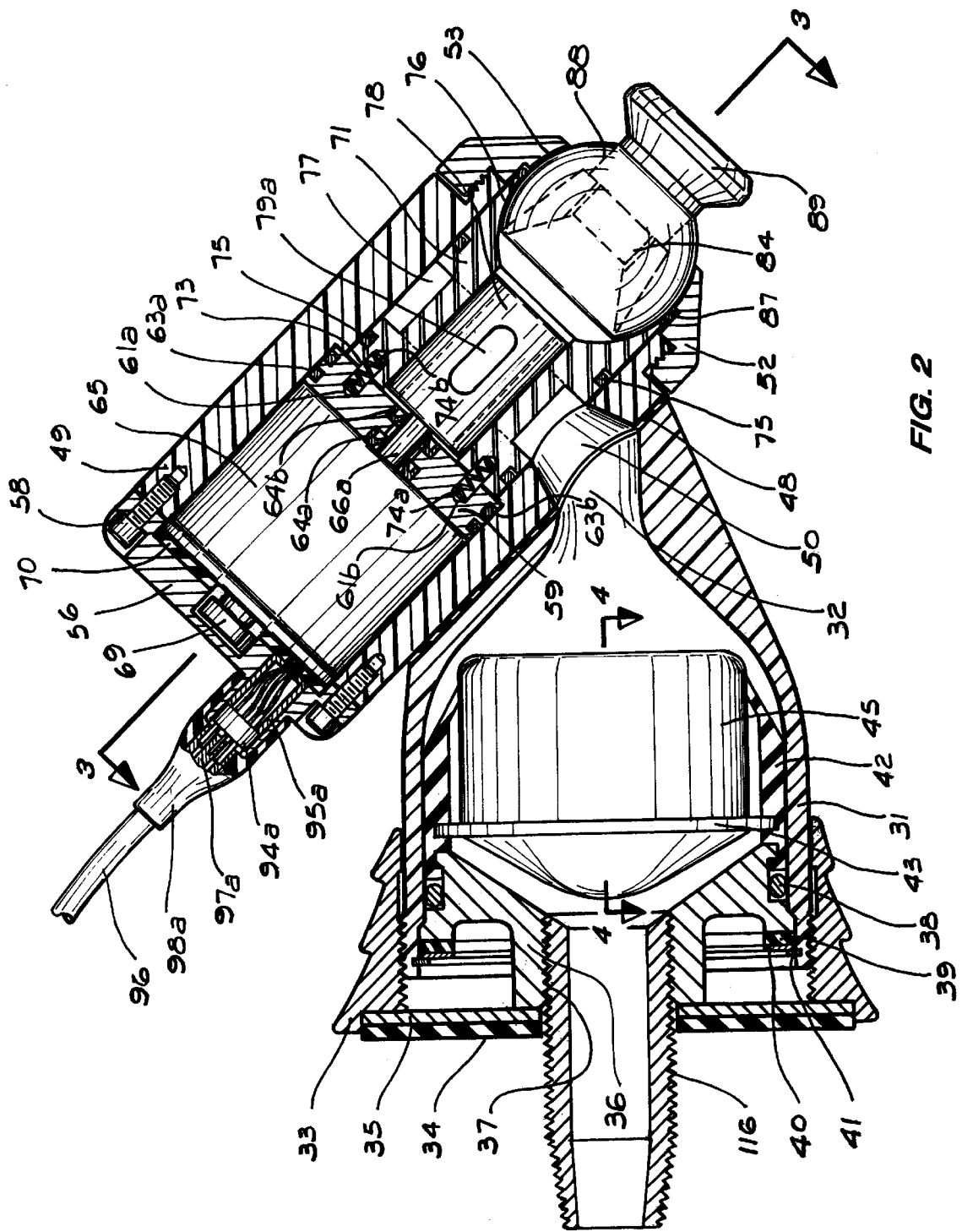
FIG. 2 is a longitudinal cross section drawing of the spray apparatus.

The major components of a pulsating spray apparatus incorporating the teachings of the present invention are illustrated as follows:

FIGS. 1, 2—An inlet port 37 is threadedly attachable to a supply pipe adaptor 116 extending from the wall within a shower stall or above a bath tub. Port 37 is at the center of end cover 36. O-ring 38 in cover 36 prevents leakage between cover 36 and outer shell 31. Cover 36 is secured by elastomeric isolator washer 39, back up ring 40 and retaining ring 41.

Shell 31 has external threads by which a threadedly adjustable stabilizing ring 33 can locate against a bath tub or shower stall wall. Ring 33 is counterbored for elastomeric isolator ring 34 and back up pad 35.

Figure 4:
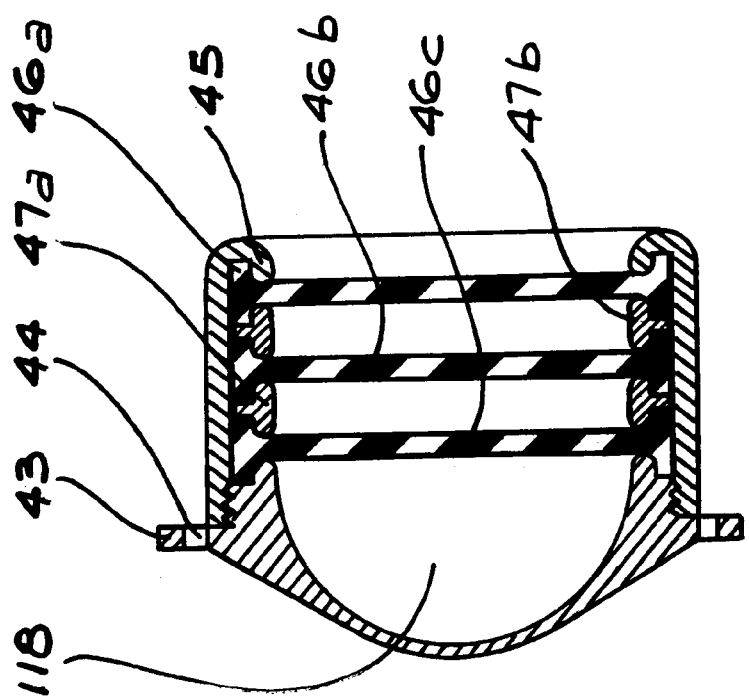
FIG. 4 is a cross section drawing of the energy absoption mechanism.
Figure 5:
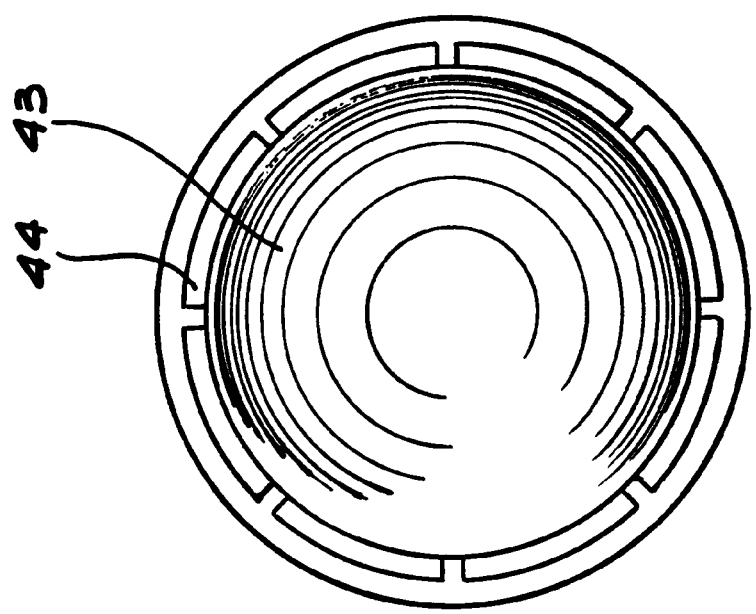
FIG. 5 is a front view drawing of the energy absorption mechanism end cap.
Figure 7:
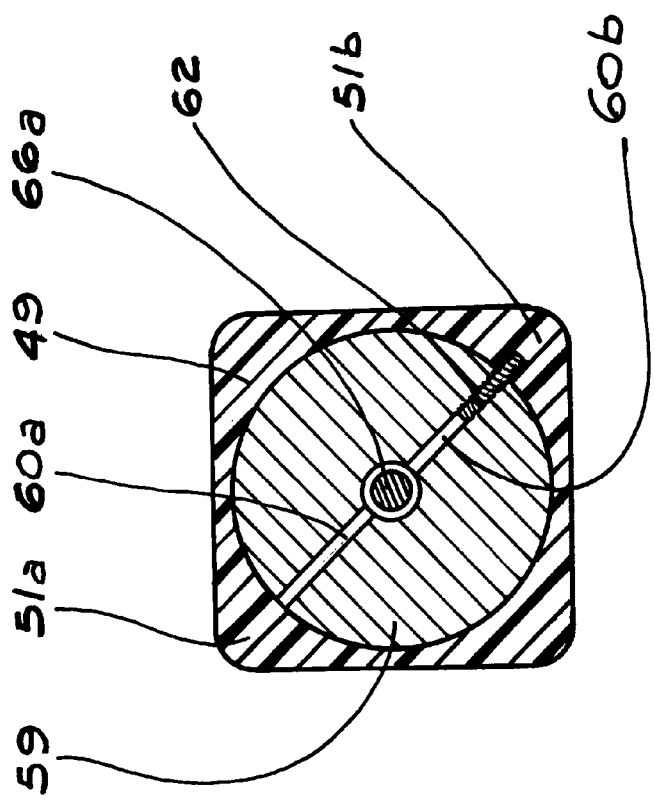
FIG. 7 is a cross section drawing of the rear cover.

FIGS. 2, 4, 5—Retaining seal 42 stretches over cover 36 and locates end cap 43. End cap housing 45 threadedly attaches to cap 43 and holds flexible membranes 46a, 46b and 46c in place within membrane spacers 47a and 47b. Membranes 46a, 46b and 46c are compressed during assembly by the inner lips of cap 43 and housing 45. Compression of the membranes permits deflection under fluid pressure while preventing fluid leakage into the interior of housing 45.

Cap 43 has multiple slots 44 for fluid to flow thru and over housing 45. Seal 42, secures cap 43 and seals over housing 45, allowing fluid flow towards outlet port 32 only.

Figure 3:
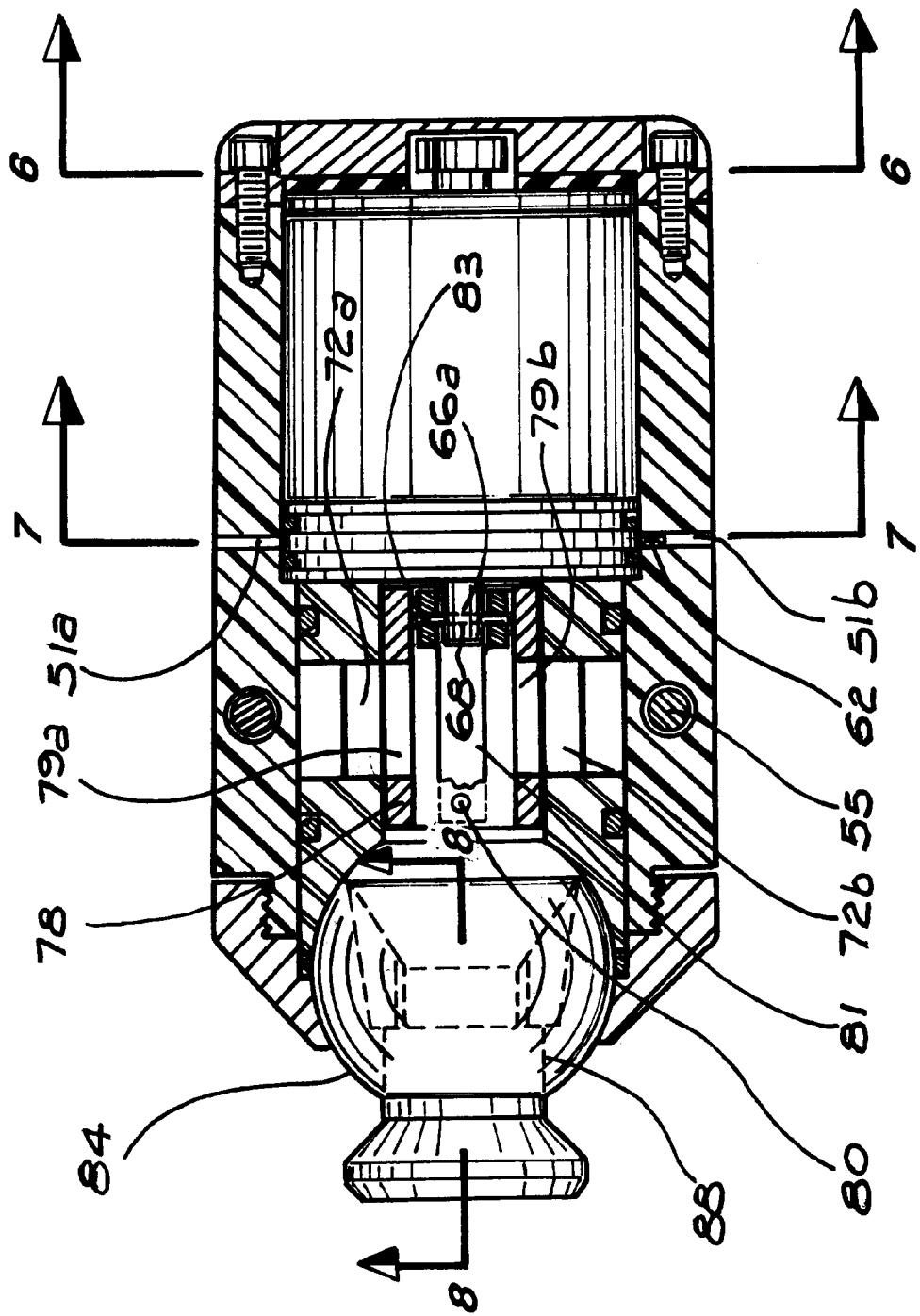
FIG. 3 is a cross section drawing of the motor housing.
Figure 6:
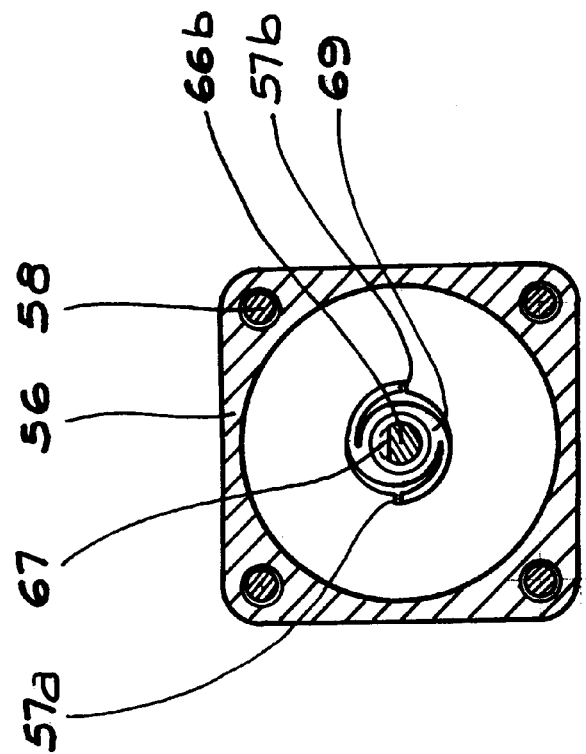
FIG. 6 is a cross section drawing of the motor housing and bulkhead spacer.

FIGS. 2, 3, 6—Motor housing 49 attaches to shell 31 by means of fasteners 55a and 55b. Inlet port 50 aligns with port 32. Gasket 48 seals the mating surfaces of shell 31 and housing 49. Housing 49 contains stepping motor 65 between bulkhead spacer 59 and rear cover 56. Cover 56 attaches to housing 49 by means of fasteners 58a, 58b, 58c and 58d, retains motor lead male connector 94a, connector spacer 95a and integrates symmetrical stops 57a and 57b.

FIGS. 2, 3, 6, 7—Motor 65 has a double ended shaft 66a, 66b. One way clutch 69 mounts on motor shaft 66b oriented by shaft flat 67, allowing rotation in clockwise direction only, stopping counterclockwise rotation within half a turn against stops 57a and 57b in cover 56. Clutch 69 is made of acetal plastic material such as Delrin; Delrin is a trademark of E. I. duPont de Nemours & Co., Wilmington, Del. Elastomeric motor pressure pad 70, between motor 65 and cover 56 loads motor 65 against bulkhead spacer 59.

Spacer 59 separates housing 49 into two chambers, preventing fluid leakage by means of dual O-rings 63a and 63b and dual motor shaft lip seals 64a and 64b. The space between seals 64a, 64b and O-rings 63a, 63b is vented to atmosphere by passageways 60a and 60b in spacer 59 and vent holes 51a, 51b in housing 49. Spacer 59 retains and orients preload springs 74a, 74b in holes 61a, 61b and is itself oriented and secured to housing 49 by setscrew 62 passing thru vent hole 51b.

FIG. 2, 3, 9, 10—Shaft 66a has a radial hole 68 receiving cross pin 83 which also engages flexible driver 81. Driver 81 is made of acetal plastic material such as Delrin. Driver 81 transmits shaft 66a rotation to inner sleeve 78 thru driving pins 82a and 82b, engaging driving holes 80a, 80b in sleeve 78. The radial location of hole 68 in shaft 66a is keyed to flat 67. Pin 83 is retained axially by the assembly of sleeve 78 to driver 81.

Sleeve 78 has two opposed, axially oriented porting slots 79a and 79b offset 90 degrees from holes 80a and 80b. Sleeve 78 rotates inside stationary sleeve 71 which has matching, porting slots 72a and 72b. Porting slots in both rotating and stationary sleeves share the same axial location when assembled in motor housing 49. The running clearance between sleeves is in the order of 0.0050 mm.

Port 50 connects with annular chamber 77 created by the assembly of sleeve 71 and housing 49. Sleeve 71 is oriented by preload springs 74a, 74b aligning with holes 61a, 61b in spacer 59, so that slots 72a, 72b are offset 90 degrees from inlet port 50 when assembled. Chamber 77 is sealed by O-rings 75a, 75b retained in sleeve 71 to prevent internal fluid leakage.

FIGS. 2, 3,—Spherical swivel joint 84 locates against mating spherical surface 76 in sleeve 71 and is retained by spherical surface 53 in retainer nut 52. Nut 52 threadedly attaches to housing 49. O-ring seal 87 prevents fluid leakage between spherical swivel joint 84, nut 52 and sleeve 71. The swivel joint is made of acetal plastic material such as Delrin and retains isolating insert 85, made of elastomeric material. Insert 85 is bonded to threaded insert 86, providing a means of attachment for discharge nozzle 89. Access hole 88 in swivel joint 84 permits fastening of nozzle 89 to insert 86.

Figure 8:
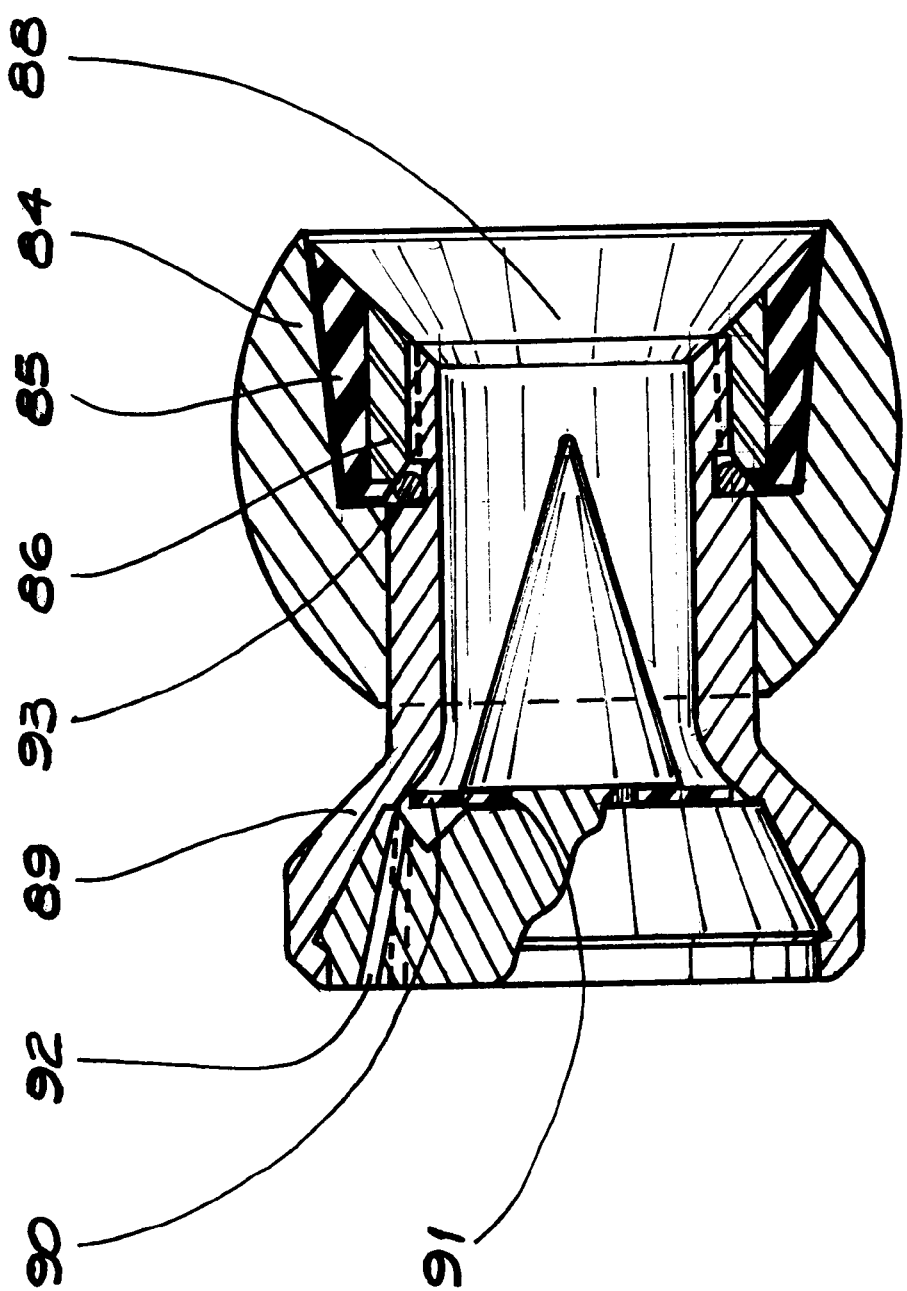
FIG. 8 is a cross section drawing of the discharge nozzle and swivel joint.
Figure 9:
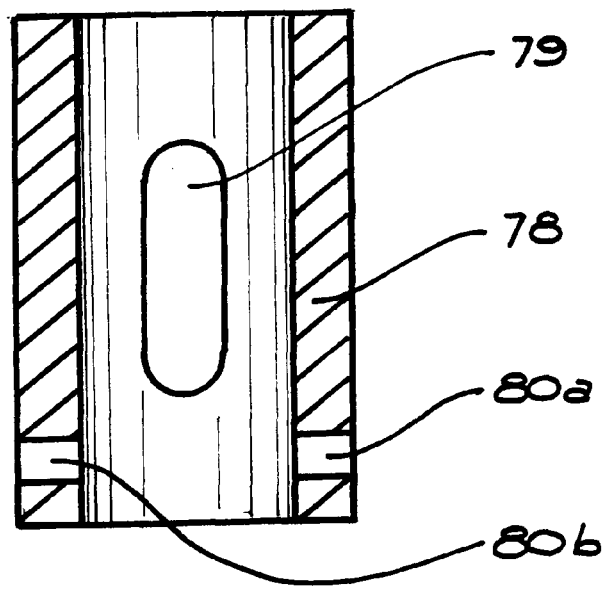
FIG. 9 is a cross section drawing of the rotating inner sleeve.
Figure 10:
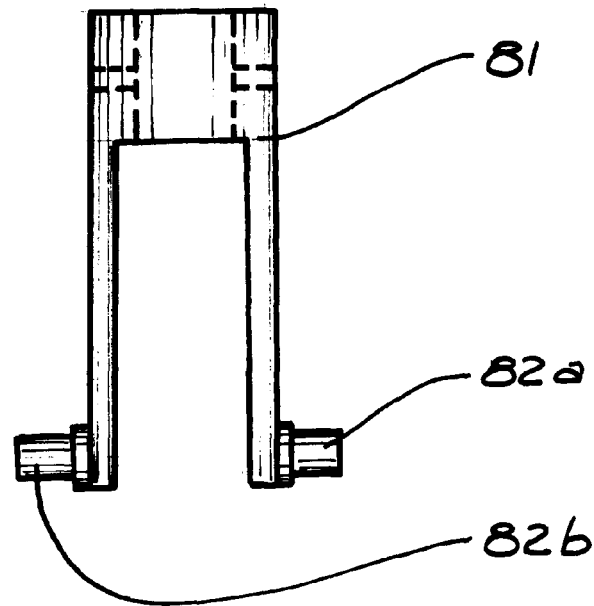
FIG. 10 is a side view drawing of the flexible driver.

FIG. 8—Nozzle 89 threadedly attach to insert 86 and prevent fluid leakage by means of O-ring 93. A flexible check disc 90 is located in circular groove 91 inside all nozzles. All nozzles share similar construction with exception of the angle of discharge, number and size of passageways 92.

FIGS. 1, 2, 11, 12, 14—The electrical connection to the motor is thru cover 56. Cover 56 houses male connector 94a. Female connector 97a terminates one end of motor cable 96 and mates with male connector 94a. Female connector 97b terminates the opposite end of cable 96 and mates with male connector 94b retained in control housing 99. Safety boot 98a, 98b make liquid tight seals with cover 56 at one end and housing 99 at the other.

Figure 11:
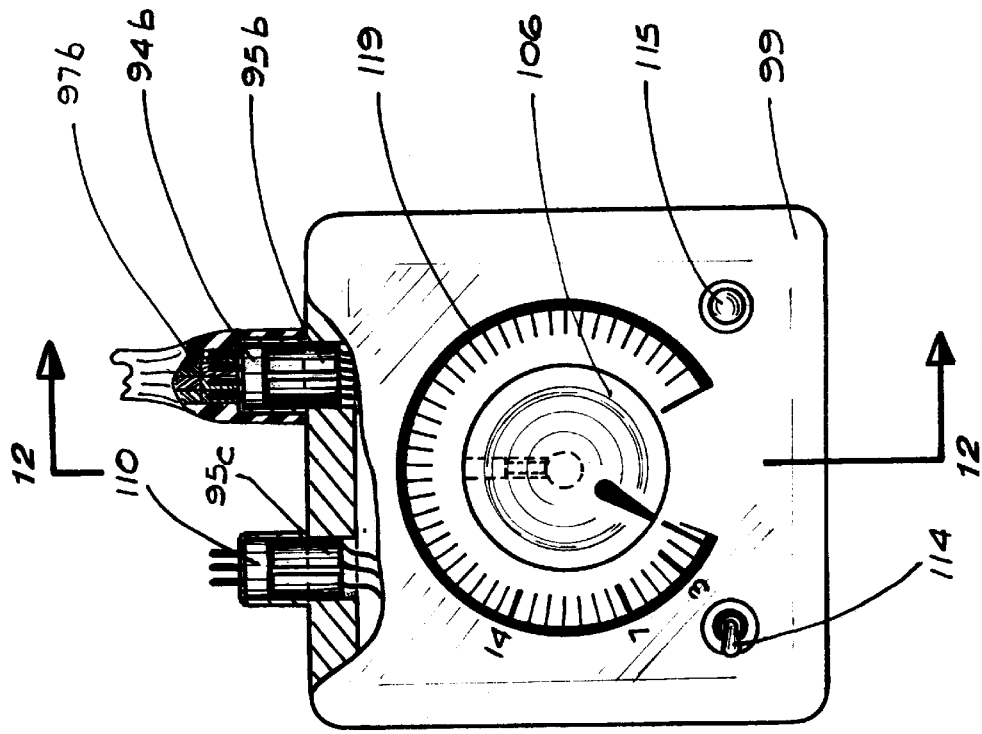
FIG. 11 is a front view drawing of the control housing.
Figure 12:
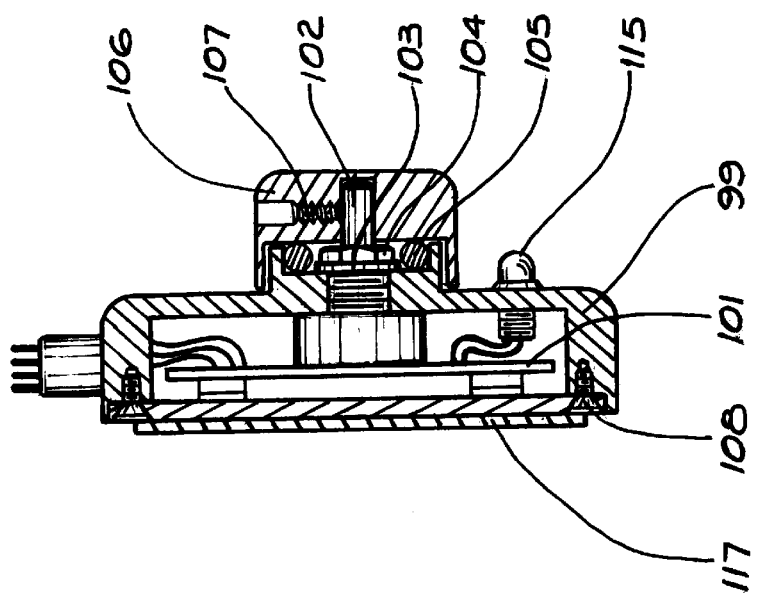
FIG. 12 is a cross section drawing of the control housing.
Figure 15:
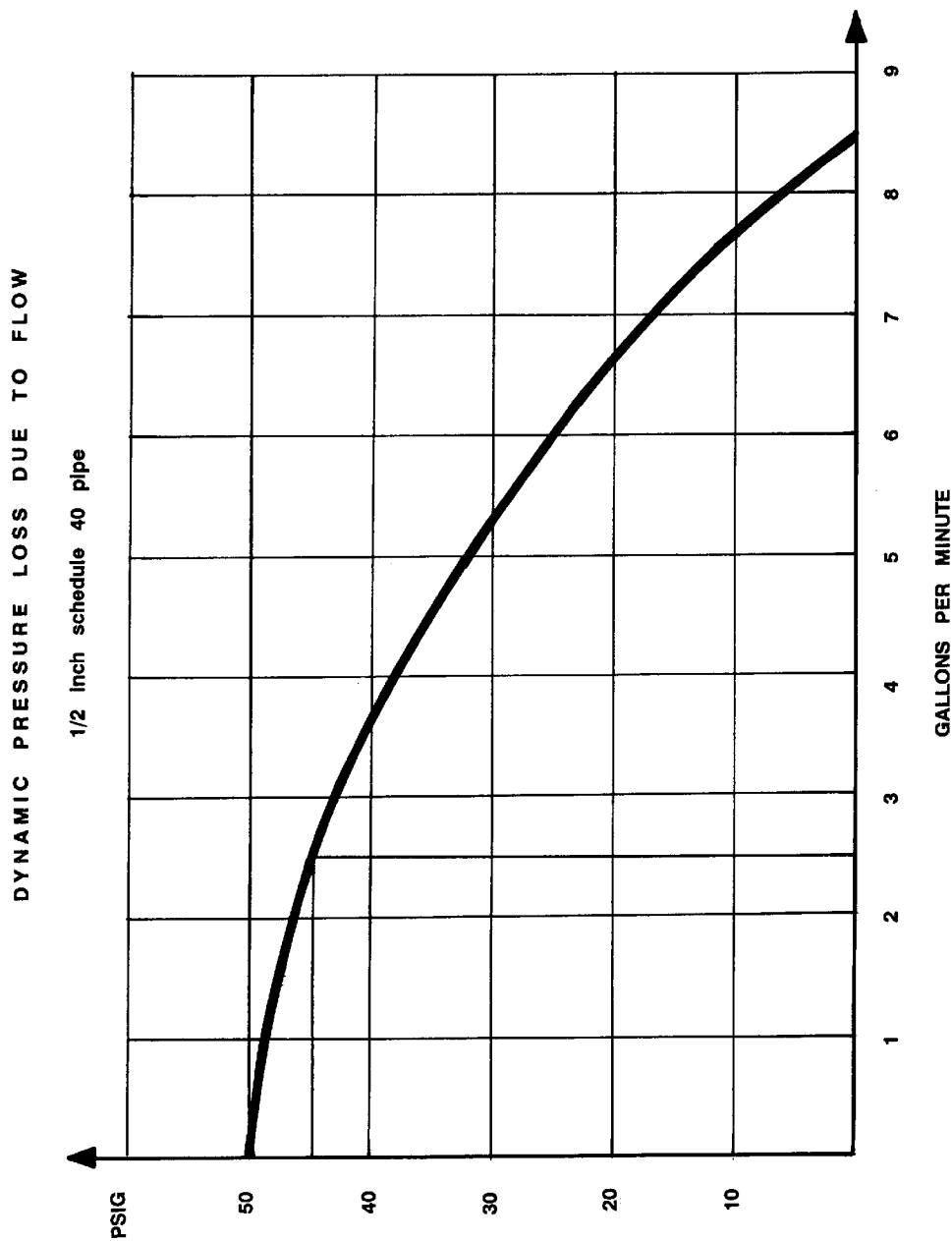
FIG. 15 is a graph showing dynamic pressure loss due to flow in a ½" schedule 40 supply pipe, 100 feet in length.
Figure 16:
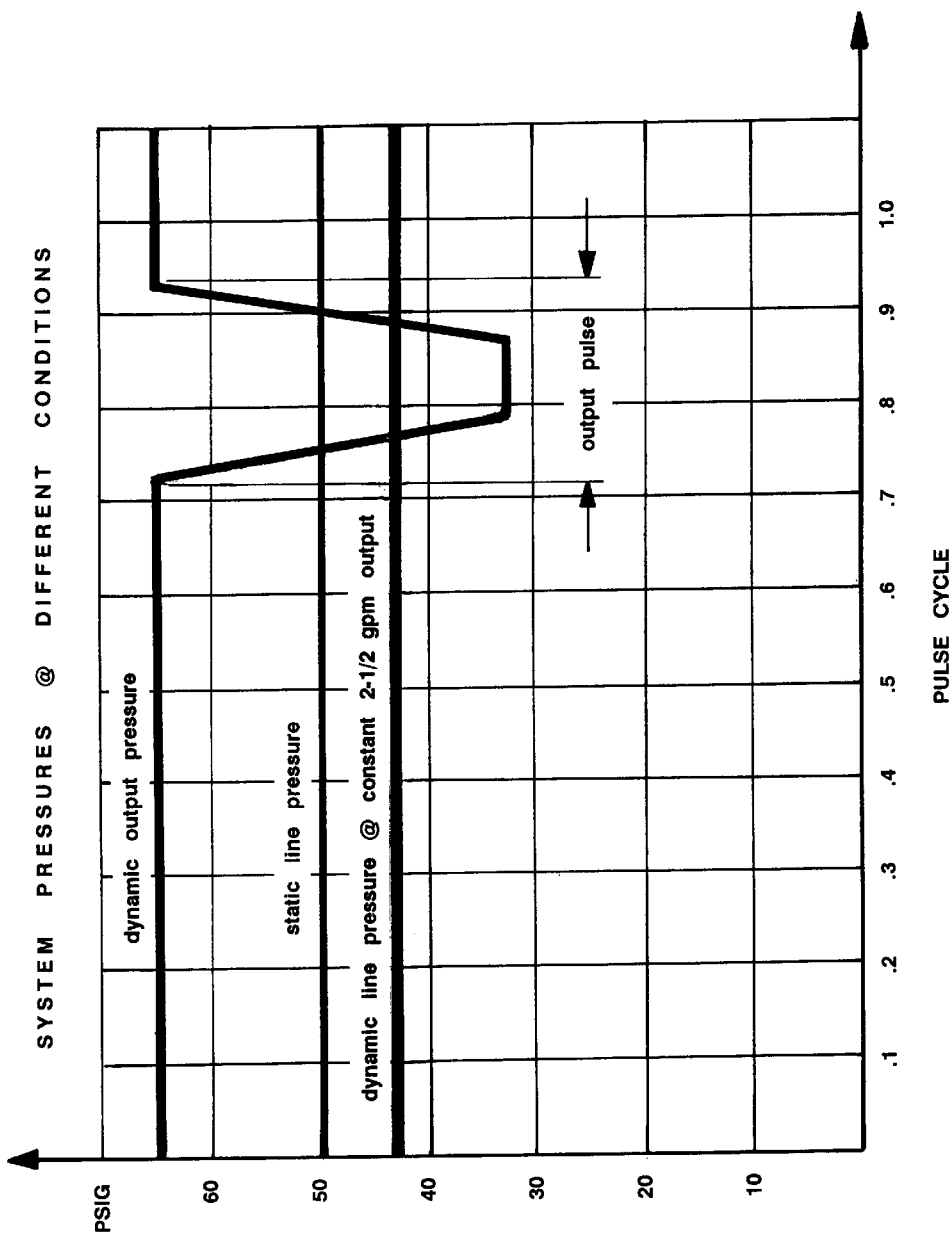
FIG. 16 is a graph showing system pressures under different conditions, including dynamic output pressures during each output cycle, dynamic line pressure under constant output flow and static line pressure.

FIGS. 11, 12, 14—Housing 99 retains male connectors 94b, 110 and connector spacers 95b, 95c, circuit board 101 and potentiometer 102. Potentiometer 102 extends thru and fastens to housing 99 with washer 103 and nut 104. Control knob 106 attaches to potentiometer 102 and by means of setscrew 107 and seals against O-ring 105 in housing 99. Back plate 100 closes off housing 99 with fasteners 108*a* thru 108*l*. Housing 99 attaches to the wall within a shower stall or bath tub by means of double adhesive tape pad 117.

FIGS. 13, 14—Power cable female connector 98 terminates dc power cable 120 at the opposite end of 24 volt dc power supply 111. Power supply 111 plugs into standard household ac current outlet by means of ac cable 102 and plug 103. Power supply 111 is a standard, U.L. approved power supply incorporating a ground fault safety interrupt circuit.

FIGS. 11, 12, 14—Selector switch 114 is a double pole, left-momentary, center-off, right-on, three position submersible switch threadedly mounted to housing 99. The switch receives dc current from power supply 111 and controls power to the circuit board, affecting the continuous clockwise or momentary counterclockwise rotation of motor 65. Pilot light 115 mounts on housing 99 and remains on when switch 114 is in the on position.

Operation—FIGS. 1, 2, 3, 4, 5, 6, 7

The manner of using the pulsating spray apparatus is similar to that used with pulsating spray devices in present use. The overall approach of the particular embodiment herein primarily illustrated is that of delivering two kinds of discharge sprays.

The first is a precisely controlled pulsating spray in which the kinetic energy of the pressurized fluid source is absorbed and retained during part of each cycle and subsequently discharged in a concentrated fluid pulse.

In operation, with selector switch 114 in the on position and a continuous fluid stream under pressure flowing thru supply pipe 116, fluid enters the apparatus thru inlet port 37, fills the volume contained within outer shell 31 and exits outlet port 32, entering motor housing 49 thru inlet port 50.

Port 50 leads to chamber 77 causing the fluid to split into two balanced streams and flow thru porting slots 72*a*, 72*b* in stationary sleeve 71 and porting slots 79*a*, 79*b* in rotating sleeve 78. The fluid then exits thru discharge nozzle 89.

As the fluid makes it way inside shell 31, from inlet port 37 to outlet port 32, it flows past retaining seal 42 and comes in contact with flexible membrane 46*a*. Seal 42 acts against membrane housing 45, preventing backflow. Membrane 46*a* deflects due to fluid pressure and transmits part of its deflection to membrane 46*b* by compressing the airspace retained between them and by actual contact. Similarly, depending on the pressure of the fluid source, membrane 46*b* may also transmit part of its deflection to membrane 46*c* which can, in turn, deflect into expansion chamber 118 contained between membrane 46*c* and end cap 43.

Slots 72*a* and 72*b* in sleeve 69, mating slots 79*a* and 79*b* in sleeve 78, all internal flow passages in the apparatus and threaded adaptor 116 are sized to exceed the capacity of conventional supply piping in order to minimize pressure losses due to flow restriction.

Fluid consumption is determined by a ratio of time between fully open and fully closed slots in sleeves 71 and 78. The ratio is a function of the physical relationship between the width of the slots, their number and their perimeter distance.

The established physical relationship is independent of rotational speed.

When slots 72*a* and 72*b* in sleeve 71 are covered by the wall of sleeve 78, the fluid flow towards nozzle 89*a* is blocked and membranes 46*a*, 46*b* and 46*c* deflect in direct proportion to the resulting increase in fluid pressure. Due to the kinetic energy of the fluid in the supply line, the energy stored by deflecting membranes 46*a*, 46*b*, 46*c*, exceeds normal static line pressure.

When slots 72*a* and 72*b* in sleeve 71 line up with mating slots 79*a* and 79*b* in sleeve 78, the blockage is relieved and the fluid moves towards discharge nozzle 89*a* aided by the energy stored in membranes 46*a*, 46*b* and 46*c*.

Sleeve 78 is driven by motor shaft 66*a* thru flexible driver 81 at a rate precisely variable from fifteen to thirty six hundred revolutions per minute. The resulting fluid interruptions, occurring every half revolution, cause discharge pulse frequencies ranging from one half to one hundred and twenty pulses per second. Control knob 106, attached to potentiometer 102 varies the rate of rotation of the motor. Dial plate 119 indicates the fluid discharge pulse rate in increments of one pulse per second across a 320 degree arc.

Membranes 46*a*, 46*b* and 46*c* rapidly oscillate with system pressure as it varies in relation to fluid motion. Each time the flow is interrupted by the rotation of sleeve 78, kinetic energy in the fluid is absorbed by further membrane deformation until fluid movement is zero and system pressure is at its highest.

Seal 42 maintains such peak energy by preventing return fluid flow and isolating shock waves from fluid supply piping. When slots 72*a* and 72*b* on sleeve 71 and mating slots 79*a* and 79*b* on sleeve 78 line up again due to the continuing rotation of sleeve 78, a concentrated fluid pulse is released, immediately propagating towards nozzle 89*a*.

Nozzle 89*a* is retained by threaded insert 86 in spherical swivel joint 84.

Preload springs 74*a*, 74*b* locate, orient and push stationary sleeve 71 against swivel joint 84, creating enough friction to prevent swivel joint 84 from drifting while allowing full directional adjustment of the discharge pulse. Swivel joint 84 locates discharge nozzle 89*a* in swivel joint access hole 88. Flexible check disc 90 snaps in place in circular groove 91 inside nozzle 89.

Disc 90 retains a column of fluid between sleeve 78 and discharge nozzle 89, minimizing dead space, reducing noise and insuring the immediate transmission and release of stored energy from membranes 46*a*, 46*b* and 46*c* thru nozzle 89. Discharge nozzles 89*a*, 89*b* and 89*c* are interchangeable, easily removable and replaceable without tools.

The second type of discharge spray is a continuous discharge in which fluid is delivered in an uninterrupted stream at a predetermined rate which meets U.S. State and Federal water consumption limits. When switch 114 in housing 99 is actuated in its momentary contact position, shaft 66 turns in a counterclockwise direction. One way clutch 69, mounted on shaft 66*b* and driven by shaft flat 67 rotates until it meets symmetrical stops 57*a* and 57*b* in rear cover 56.

Shaft 66*a*, at the opposite end of shaft 66*b* simultaneously rotates sleeve 78 so that porting slots 79*a* and 79*b* partially overlap porting slots 72*a* and 72*b* in sleeve 71, producing two opposed and equally controlled fluid openings and a continuous, restricted fluid discharge volume from nozzle 89*a*. Sleeve 78 retains its position and the restricted fluid discharge continues when switch 114 is released from its momentary actuation. Switch 114 then reverts to its center off position, interrupting current flow to electronic circuit board 101.

Actuation of the switch to its on position permits the motor to again rotate in a clockwise direction. The rotation rate of the motor in both clockwise and counterclockwise directions depends on the position of control knob 106. Pilot light 115 remains on when switch 114 is in the on position.

Summary, Ramifications and Scope

Accordingly, the reader will see that the apparatus of the invention provides a convenient method of producing a change of consciousness in a human being that is supportive of daily activities. In addition, the apparatus provides an unmatched body massage, delivering the strongest possible spray out of a common water supply line. Furthermore, its operation under either pulsating or continuous discharge mode meets Federal and State water consumption guidelines.

While my above description contains many specificities, they should not be construed as limitations of the scope of the invention, but rather as an exemplification of one preferred embodiment thereof.

Many other variations are possible. For example, the energy absorption mechanism can be remotely placed in the supply line, or external to the main body of the spray apparatus; the motor can be of different type and its location external to the spray apparatus; the rotating sleeve can be made as a disc and the shape of the slots altered to produce the same effect, etc.

Thus the scope of the invention should be determined by the appended claims and their legal equivalents, rather than by the examples given.

I claim:

1. A method for producing a variably pulsed fluid discharge from a flowing fluid stream supplied under pressure by a pipeline, utilizing valve means and comprising the steps of:

(a) repeatedly blocking and unblocking the flow of said flowing fluid stream, wherein one blocking plus one unblocking constitutes a cycle, wherein time elapses during said cycle, wherein the elapsed time during one blocking plus the elapsed time during one unblocking establishes a cyclic frequency, and wherein repeatedly blocking and unblocking the fluid stream produces a cyclic fluid discharge, (b) establishing the portion of cycle time elapsed during blocking in relation to the portion of cycle time elapsed during unblocking as a constant, wherein the fluid throughput of a cycle determines the fluid throughput of said valve means, and (c) varying the cycle time so that the proportion of cycle time elapsed blocking and unblocking the fluid stream during each cycle remains constant, wherein the cyclic fluid dicharge of said valve means is inversely proportional to its frequency, and preserves the established fluid throughput of said valve means, whereby said method produces a variably pulsed fluid discharge having a controlled fluid throughput independent of the frequency of the pulsed discharge.

2. A method for producing a pulsed fluid discharge from a flowing fluid stream supplied under pressure by a pipeline, utilizing in combination, check valve means, resilient element means and valve means, and comprising the steps of:

(a) repeatedly blocking and unblocking said flowing fluid stream using said valve means, (b) entrapping the fluid in a chamber between said valve means and said check valve means during said valve means blocking configuration, (c) expanding the volume of fluid in the chamber, wherein said resilient element means increase the volume of the chamber during said valve means blocking configuration, (d) confining the expanded volume of fluid in the chamber with said check valve means, and (e) releasing the fluid in the chamber during said valve means unblocking configuration, whereby pressure peaks are produced in said fluid chamber in direct proportion to the kinetic energy of said flowing fluid stream and the blocking rate of saidcheck valve means and discharged as discrete fluid pulses each time said valve means revert to an unblocking configuration.

3. A method for producing a change of consciousness in a mammal, from an existing present and known state of consciousness, as verified by the mammal's brainwaves frequency, to another similarly known and similarly verifiable state of consciousness, utilizing a fluid stream supplied under pressure by a pipeline and valve means, and comprising the steps of:

(a) repeatedly blocking and unblocking said fluid stream with said valve means, wherein one instance of said blocking and unblocking constitutes a cycle, wherein the time elapsed during one said blocking and unblocking establishes a cyclic frequency, (b) blocking the fluid stream as to produce a rapid increase in pressure within said valve means, wherein said rapid increase in pressure causes a sharp pressure peak commonly referred to as water hammer, (c) unblocking the fluid stream as to release said increased pressure in an intensified fluid discharge, (d) stimulating sensory organs residing in the skin of said mammal with said intensified discharge, wherein said stimulation captures the mammal's attention, and (e) setting the frequency of said cyclic fluid discharge so it replicates the known frequency of said other state of consciousness, whereby said method produces a change in consciousness by cyclically increasing the intensity of the fluid stream beyond the pressure normal to the supply pipeline, and releasing an intensified discharge having the capacity to saturate the cognitive ability of sensory organs in the skin, thus capturing said mammal's attention and inducing said mammal's brainwaves into a synchronous frequency with the cyclic frequency of the intensified discharge.

4. A pulsating fluid mechanism supplied by a pipeline containing a flowing fluid stream under pressure comprising:

(a) a housing having inlet and outlet fluid ports connected by fluid passageways, valve means for sequentially closing and opening said fluid passageways, producing pressure peaks and fluid pulses, said valve means positioned in the fluid passageways between said inlet and outlet fluid ports, (b) resilient element means for absorbing the pressure peaks produced by said valve means by expanding the volume of a fluid chamber, said resilient element means located in the fluid passageways between said valve means and said fluid inlet port, and (c) check valve means for confining said pressure peaks within said fluid chamber, thus preventing propagation of pressure peaks towards the inlet fluid port, said check valve means located in the fluid passageways between said inlet fluid port and said resilient element means, and (c) said fluid chamber defined by said valve means, said fluid passageways, said check valve means and said resilient element means, whereby, said valve means produce pressure peaks by interrupting the flowing fluid stream, said resilient element means absorb pressure peaks by expanding the volume in said chamber, said check valve means confine pressure peaks, preventing propagation towards the fluid inlet port, and subsequently, said valve means release pressure peaks as discrete fluid pulses.

5. The pulsating fluid mechanism according to claim 4 further comprising means for powering said valve means independently of said fluid supply.

6. The pulsating fluid mechanism according to claim 4 further comprising a fluid flowthrough capacity equal to or exceeding that of said supply pipeline.

7. The pulsating fluid mechanism according to claim 4 further comprising means for sequentially closing then opening said fluid passageways between ½ and 120 times per second.

8. The pulsating fluid mechanism according to claim 4 further comprising means for electronically controlling the sequential closing and opening frequency of said fluid passageways.

9. The pulsating fluid mechanism according to claim 4 further comprising means for storing and executing any one of several closing and opening frequencies of said fluid passageways.

10. The pulsating fluid mechanism according to claim 4 further comprising:
 (a) a hollow outer shell, having an axially elongated cylindrical shape, with a large opening in one end and a tapering wall towards a smaller exit opening at the opposite end, said outer shell having an open end and means for attaching a motor housing at the opposite smaller end,
 (b) an end cover attached to said outer shell, said end cover having an inlet port with threaded means of attachment to said pipeline, said end cover having a circular groove utilized for retaining sealing means,
 (c) said sealing means sealing the perimeter of said end cover against said outer shell, said sealing means stretching over said circular groove and over the perimeter of a circular end cap,
 (d) said circular end cap having a plurality of fluid passageways near its outer perimeter and means for threadedly mounting a cylindrical housing, said sealing means forming a one way fluid passageway against said cylindrical housing,
 (e) said cylindrical housing having a chamber utilized for retaining said pressure peaks and preventing said peaks' propagation upstream into said pipeline,
 (f) said cylindrical housing holding a stack of flexible membranes by means of an inner lip formed on its open end, said cylindrical housing holding the stack of membranes separated by spacers, exposing the top membrane in the stack to the fluid flow and sealing off the stack from said fluid by compressing the flexible members between said spacers and said end cap,
 (f) said stack of flexible membranes made of a material capable of deforming progressively in response to the cyclically varying pressure of said fluid,
 (h) said motor housing having a square outer shape enclosing a cylindrical chamber split into two chambers by a bulkhead spacer, one of the chambers receiving a motor and a cover, said motor having a shaft whose length extends through said bulkhead spacer, said cover enclosing and retaining said motor in the one chamber, the second of said chambers enclosing a fluid inlet hole, said inlet hole supplying fluid to rotating inner sleeve located in the chamber within a stationary outer sleeve, said inner sleeve discharging fluid through a spherical swivel joint held against said motor housing by a threadedly mounted retainer nut,
 (i) said bulkhead spacer having redundant sealing means, sealing against said motor housing and against the shaft on said motor, said redundant seals having a vent to atmospheric pressure,
 (j) said stationary outer sleeve having multiple, axially oriented, elongated slots, said slots width and length enclosing an area which when multiplied by the number of slots results in a total area in excess of the cross section area of the fluid supply pipeline,
 (k) said rotating inner sleeve being driven by said motor through rotary transmission means, said inner sleeve having multiple axially oriented elongated slots in similar fashion to the slots in said stationary outer sleeve, the major diameter of said rotating sleeve creating a common boundary perimeter with the minor diameter of said stationary sleeve, the length of said boundary perimeter sized in proportion to the width of said elongated slots so that the motion of said inner sleeve produces an alternating complete blockage and unrestricted full passage of said fluid stream, said alternating cycle possessing a cyclic ratio between the open and closed portions of the cycle, said ratio resulting from the actual physical configuration of said sleeve and elongated slots, said cyclic ratio establishing fluid consumption irrespective of the speed of said rotation,
 (l) said spherical swivel joint being retained between said stationary sleeve and said threadedly mounted retainer nut, said swivel joint having attachment means for a discharge nozzle, said retainer nut having peripheral sealing means against said swivel joint, and
 (m) a discharge nozzle attached to the swivel joint and having pressure sensitive flow control means for retaining a column of fluid at ambient pressure between said nozzle and said rotating inner sleeve,
whereby when said concentrated pulses are released, the discharge occurs immediately, with less noise and less loss of force.

11. The pulsating fluid mechanism according to claim 4 further comprising means for controlling fluid flow so that the rate of discharge of said flowing fluid stream is inversely proportional to its discharge frequency, whereby said pulsating fluid mechanism sustains a constant fluid consumption regardless of the rate at which said fluid pulses are released.

12. The pulsating fluid mechanism according to claim 4 further comprising:
 (a) said housing having means for attachment to said supply pipeline,
 (b) said housing having means for restraining movement and isolating vibration,
whereby said restraining means exert a steadying force and prevent movement under the force of said fluid pulse discharge.

13. The pulsating fluid mechanism according to claim 4 further comprising means for selectively operating said valve means in two different modes, the first mode requiring said valve means to repeatedly close and open and the second mode requiring said valve means to remain open, whereby a human being may select either a pulsating or a continuous fluid discharge.

14. The pulsating fluid mechanism according to claim 4 further comprising means for causing said valve means to partially close said fluid passageways, whereby the apparatus produces a flow restricted continuous fluid discharge that meets established consumption standards.

15. The pulsating fluid mechanism according to claim 4 further comprising means for attaching a spherical swivel joint at a location downstream from said valve means, said swivel joint having means for securing and orienting a discharge nozzle, whereby a human being may aim, remove and replace said discharge nozzle without requiring the use of tools.

16. The pulsating fluid mechanism according to claim 4 further comprising manual means for causing said valve means to open said fluid passageways, whereby a human being may obtain a fluid discharge from a disabled apparatus having said valve means in a closed position.

\* \* \* \* \*